(12) United States Patent
Fukuda et al.

(10) Patent No.: US 9,775,495 B2
(45) Date of Patent: Oct. 3, 2017

(54) OPERATION DEVICE FOR INTO-BORE INTRODUCTION DEVICE, AND INTO-BORE INTRODUCTION DEVICE

(71) Applicant: OLYMPUS CORPORATION, Hachioji-shi, Tokyo (JP)

(72) Inventors: Hiroyuki Fukuda, Machida (JP); Yasuo Funakoshi, Hachioji (JP); Kota Sugaya, Kunitachi (JP); Kenji Tajima, Hachioji (JP); Yuki Hoshino, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/131,875

(22) Filed: Apr. 18, 2016

(65) Prior Publication Data

US 2016/0227983 A1 Aug. 11, 2016

Related U.S. Application Data

(63) Continuation of application No. PCT/JP2014/082317, filed on Dec. 5, 2014.

(30) Foreign Application Priority Data

Dec. 13, 2013 (JP) ................................ 2013-258453

(51) Int. Cl.
*A61B 1/04* (2006.01)
*A61B 1/005* (2006.01)
(Continued)

(52) U.S. Cl.
CPC ........ *A61B 1/0052* (2013.01); *A61B 1/00039* (2013.01); *A61B 1/0661* (2013.01); *A61B 1/12* (2013.01); *G02B 23/2476* (2013.01)

(58) Field of Classification Search
CPC .................. A61B 1/00066; A61B 1/00068
(Continued)

(56) References Cited

U.S. PATENT DOCUMENTS 4,566,437 A * 1/1986 Yamaguchi .......... A61B 1/0055
600/131
4,616,630 A * 10/1986 Arakawa .............. A61B 1/0052
600/131
(Continued)

FOREIGN PATENT DOCUMENTS

JP S63-84116 U 6/1988
JP H06-142030 A 5/1994
(Continued)

OTHER PUBLICATIONS

Jun. 23, 2016 International Preliminary Report on Patentability issued in International Application No. PCT/JP2014/082317.
(Continued)

*Primary Examiner* — Matthew J Kasztejna
(74) *Attorney, Agent, or Firm* — Oliff PLC (57) ABSTRACT

An operation device for an into-bore introduction device, includes: a projecting portion formed to project from a grasping section in a radial direction to a longitudinal axis of the grasping section, in a surface between a surface on which a bending operation knob is disposed and a surface on which operator's palm abuts to grasp the grasping section, in the grasping section; a pressing switch disposed on the projecting portion; and an inclined surface formed distantly by as much as a predetermined distance from the pressing switch, and in which an amount of the inclined surface to project outside in the radial direction is decreased on an insertion section side of the projecting portion.

12 Claims, 9 Drawing Sheets

(51) Int. Cl.
*G02B 23/24* (2006.01)
*A61B 1/06* (2006.01)
*A61B 1/12* (2006.01)
*A61B 1/00* (2006.01)

(58) Field of Classification Search
USPC .......................................................... 600/131
See application file for complete search history.

(56) References Cited

U.S. PATENT DOCUMENTS

| | | | | |
|---|---|---|---|---|
| 5,447,148 A * | 9/1995 | Oneda | ................ | A61B 1/00091 600/131 |
| 6,520,908 B1 * | 2/2003 | Ikeda | ................ | A61B 1/00121 600/110 |
| 8,092,373 B1 * | 1/2012 | Papouras | ........... | A61B 1/00066 600/102 |
| 8,118,732 B2 * | 2/2012 | Banik | ................ | A61B 1/00059 600/117 |
| 8,858,427 B2 * | 10/2014 | Yamazaki | .......... | A61B 1/00066 600/104 |
| 2004/0082835 A1 * | 4/2004 | Ishizuka | ............ | A61B 1/00068 600/133 |
| 2004/0176660 A1 * | 9/2004 | Abe | ................... | A61B 1/00059 600/101 |
| 2007/0249904 A1 * | 10/2007 | Amano | ............... | A61B 1/00052 600/131 |
| 2008/0086031 A1 | 4/2008 | Mitsuya | | |
| 2012/0165605 A1 * | 6/2012 | Yamazaki | .......... | A61B 1/00066 600/106 |
| 2013/0012780 A1 * | 1/2013 | Nakamura | ........... | A61B 1/0052 600/122 |
| 2014/0100424 A1 * | 4/2014 | Hoshino | ................ | H01H 13/14 600/118 |
| 2014/0187864 A1 * | 7/2014 | Kubo | ................. | A61B 1/00066 600/139 |
| 2014/0200513 A1 * | 7/2014 | Koitabashi | ......... | A61B 1/00066 604/95.04 |
| 2015/0057537 A1 * | 2/2015 | Dillon | .................. | A61B 1/0014 600/431 |
| 2016/0242629 A1 * | 8/2016 | Hijihara | ............ | A61B 1/0052 |

FOREIGN PATENT DOCUMENTS

| | | |
|---|---|---|
| JP | 2004-141331 A | 5/2004 |
| JP | 2008-092968 A | 4/2008 |

OTHER PUBLICATIONS

Feb. 24, 2015 Search Report issued in International Patent Application No. PCT/JP2014/082317.

* cited by examiner

OPERATION DEVICE FOR INTO-BORE INTRODUCTION DEVICE, AND INTO-BORE INTRODUCTION DEVICE

CROSS-REFERENCE TO RELATED APPLICATIONS

This application is a Continuation application of PCT Application No. PCT/JP2014/082317, filed Dec. 5, 2014 and based upon and claiming the benefit of priority from prior Japanese Patent Application No. 2013-258453, filed Dec. 13, 2013, the entire contents of all of which are incorporated herein by reference.

BACKGROUND OF THE INVENTION

1. Field of the Invention

This invention relates to an operation device for an into-bore introduction device to introduce an insertion section into a bore, and the into-bore introduction device.

2. Description of the Related Art

In an operation device for an into-bore introduction device (an operation device of an endoscope) which is disclosed in, for example, Jpn. Pat. Appln. KOKAI Publication No. 2004-141331 and Jpn. Pat. Appln. KOKAI Publication No. 2008-92968, there is a stepped portion formed as a substantially rectangular surface (a projecting surface) between a first grasping portion and a second grasping portion. The operation device is grasped in a stabilized state by placing a middle finger and a ring finger on a lower side of the stepped portion.

BRIEF SUMMARY OF THE INVENTION

According to one embodiment of the present invention, an operation device for an into-bore introduction device, includes: a grasping section that is connected to a proximal portion of an insertion section to be inserted into a bore, and is to be grasped by an operator to operate the insertion section; a bending operation knob that is disposed on the grasping section and that bends a bending portion of the insertion section; a projecting portion that is formed to project from the grasping section in a radial direction to a longitudinal axis of the grasping section, in a surface between a surface on which the bending operation knob is disposed and a surface on which operator's palm abuts to grasp the grasping section, in the grasping section; a pressing switch that is disposed on the projecting portion and that operates the insertion section; and an inclined surface that is formed distantly by as much as a predetermined distance from the pressing switch, and in which an amount of the inclined surface to project outside in the radial direction is decreased on an insertion section side of the projecting portion.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Hereinafter, embodiments of this invention will be described with reference to the drawings.

A first embodiment will be described with reference to FIG. 1 to FIG. 4.

Figure 1:
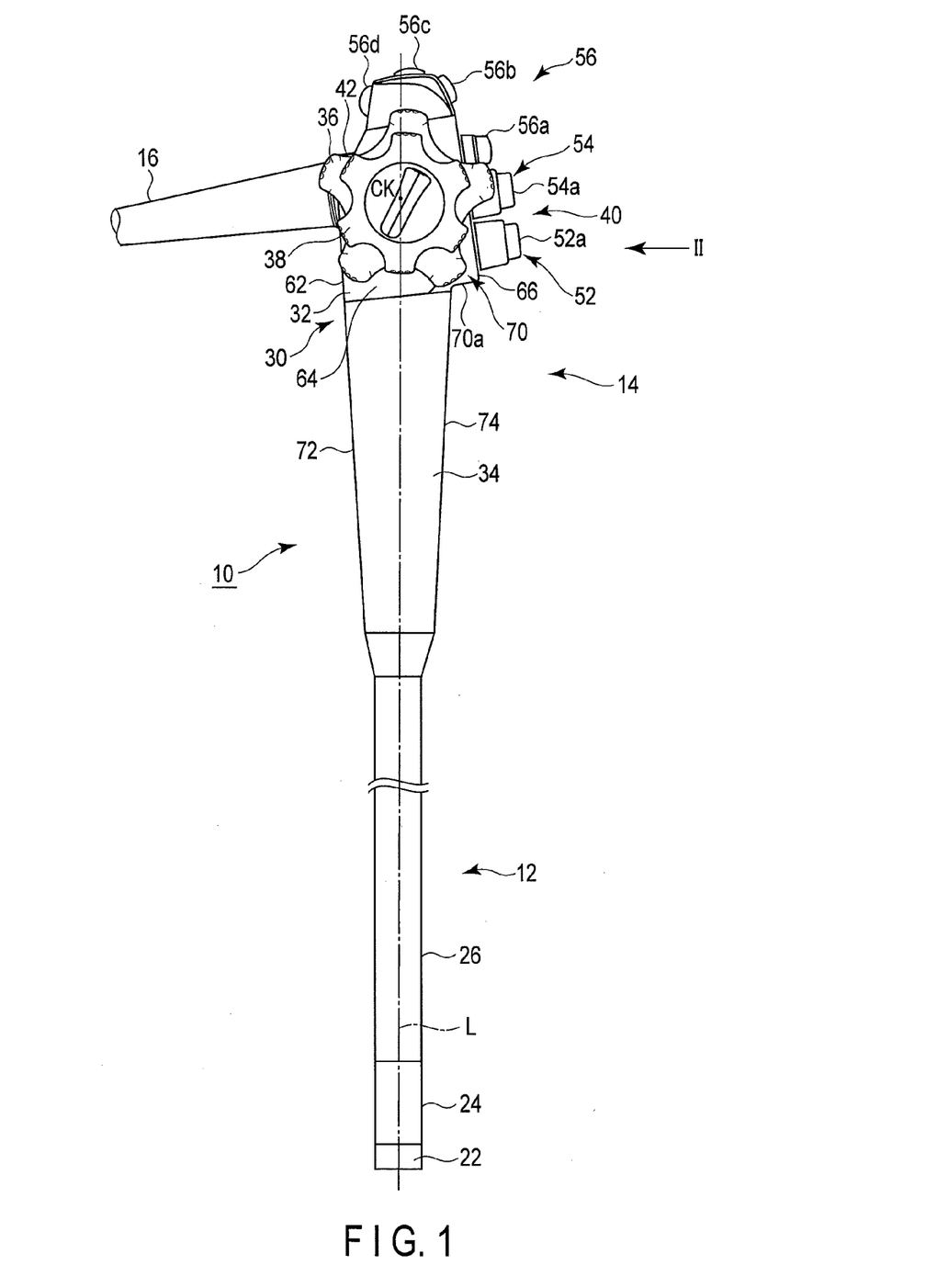
FIG. 1 is a schematic view showing an endoscope (an into-bore introduction device) according to first and second embodiments.

As shown in FIG. 1, in this embodiment, an endoscope 10 will be described as an example of an into-bore introduction device.

The endoscope (the into-bore introduction device) 10 includes an insertion section 12 to be inserted into a bore, an operation device 14 to be grasped with one of a user's hands, especially the left hand for use in suitably operating the endoscope 10 including the insertion section 12, and a universal cord 16 to be connected to an unshown control unit that controls the endoscope 10.

Although not shown in the drawing, the endoscope 10 includes therein a known illumination optical system that illuminates the inside of the bore, and a known observation optical system in which the inside of the bore illuminated with the illumination optical system is imaged and observed. The endoscope 10 further includes a known air supply/water supply/suction unit capable of washing an unshown objective lens and the like of the observation optical system and sucking a biological tissue, blood and the like.

The insertion section 12 includes a distal hard portion 22, a bending portion 24 and a tubular member 26 having a flexibility, in order from a distal portion to a proximal portion of the insertion section 12. As the tubular member 26, a member having the flexibility, e.g., a flexible tube of an insertion section of a so-called flexible endoscope is preferably used, but a hard tube that is made of a metal material such as a stainless steel alloy material and does not have the flexibility may be used.

The operation device 14 is provided in the proximal portion of the insertion section 12. The insertion section 12 and the operation device 14 are present on a common longitudinal axis L. Specifically, the insertion section 12 is coupled with a second grasping portion 34 that will be described later, and extended to a side opposite to a first grasping portion 32.

Figure 2:
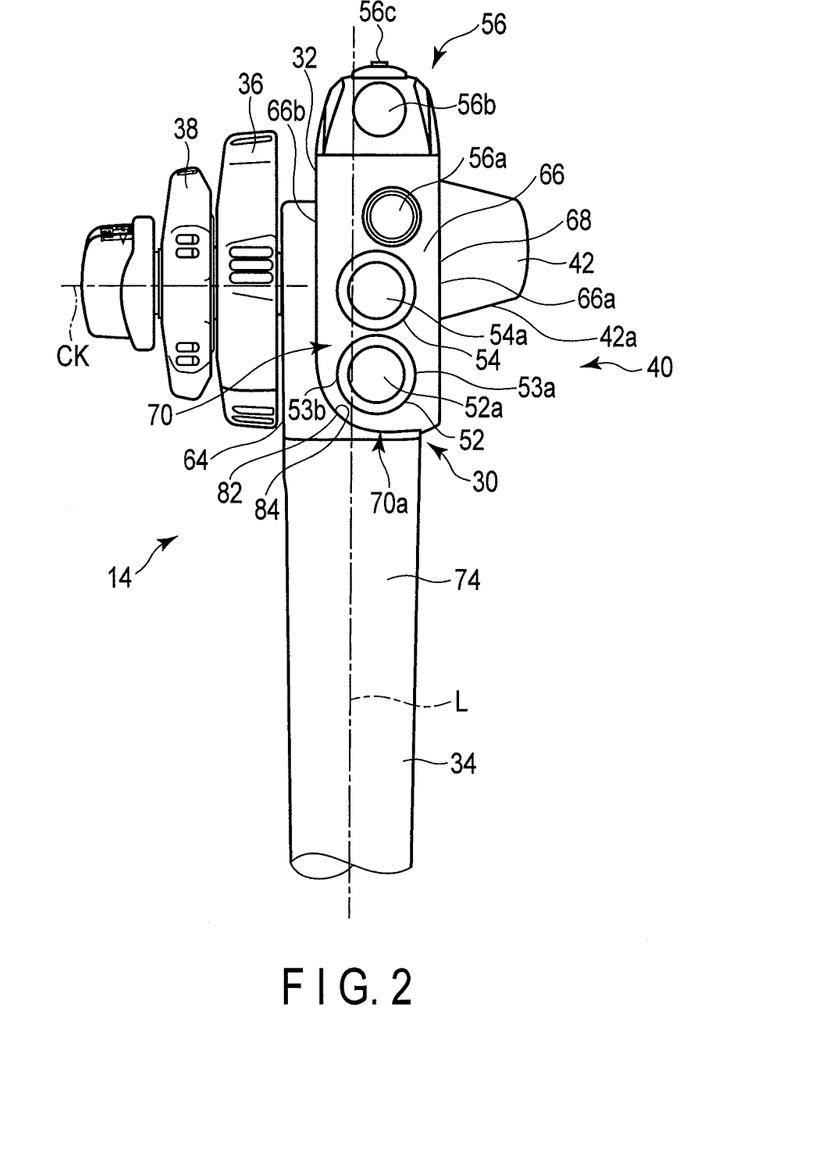
FIG. 2 is a schematic view showing an operation device of the endoscope (the into-bore introduction device) according to the first embodiment seen from a direction of an arrow II in FIG. 1.

As shown in FIG. 1 and FIG. 2, the operation device 14 includes a grasping section 30 to be grasped by an operator to operate the insertion section 12, a UD bending operation knob 36, an RL bending operation knob 38, a pressing switch assembly 40, and a connector 42 from which the universal cord 16 is extended outside. The grasping section 30 includes a first grasping portion (an upper grasping portion) 32 and a second grasping portion (a lower grasping portion) 34.

The longitudinal axis L of the insertion section 12 is present on a central axis of the insertion section 12. The second grasping portion 34 of the operation device 14 is positioned closer to the insertion section 12 than the first grasping portion 32 along the longitudinal axis L.

The pressing switch assembly 40 includes first and second pressing valve units (pressing switches) 52 and 54, and a switch unit 56.

The first pressing valve unit 52 as the pressing switch is disposed on a third surface 66 that will be described later, present on a side (a lower side) close to the second grasping portion 34 and the insertion section 12, and is used to perform air supply or water supply to discharge a gas or a liquid from a distal end of the distal hard portion 22 of the insertion section 12. The second pressing valve unit 54 is present on a side (an upper side) away from the insertion section 12, and is used to suck the biological tissue, blood or the like present at the distal end of the distal hard portion 22 of the insertion section 12. The first and second pressing valve units 52 and 54 are parts of the abovementioned known air supply/water supply/suction unit inserted from a distal end of the insertion section 12 of the endoscope 10 into a distant end of the universal cord 16 from the operation device 14. It is to be noted that the first and second pressing valve units 52 and 54 according to this embodiment preferably have the same size and the same appearance in shape. Additionally, the first and second pressing valve units 52 and 54 preferably have a cylindrical shape.

Additionally, on the upper side of the second pressing valve unit 54 in the first grasping portion 32, the switch unit 56 having switches (the pressing switches) 56a, 56b, . . . is disposed. Functions of the switches 56a, 56b, . . . are suitably set. One of the switches of the switch unit 56 has, for example, a function set by the unshown control unit of the endoscope 10 and used to image a static image. Additionally, one of the other switches has, for example, a function set by the unshown control unit and used to switch illumination light to usual light (incandescent light) or special light (e.g., fluorescent light).

The first grasping portion 32 includes, as an outer peripheral surface, a first surface (a user facing surface) 62, a second surface (an operation knob disposing surface) 64, a third surface (a pressing valve unit disposing surface) 66 and a fourth surface (a universal cord disposing surface) 68 in a peripheral direction around the longitudinal axis L. A boundary between the first surface 62 and the second surface 64, a boundary between the second surface 64 and the third surface 66, a boundary between the third surface 66 and the fourth surface 68 and a boundary between the fourth surface 68 and the first surface 62 are formed into smoothly curved surfaces via each of which both the faces are continuous with each other. The outer peripheral surface of the first grasping portion 32 along the peripheral direction around the longitudinal axis L is formed into an annular shape in which the first to fourth surfaces 62, 64, 66 and 68 cooperate. The outer peripheral surface of the first grasping portion 32, i.e., a shell is preferably formed into, for example, a tubular shape having a substantially rectangular transverse cross section. The second grasping portion 34 includes, as an outer peripheral surface, a user facing surface (a fifth surface) 72 continuous with the first surface 62 and a grip surface (a sixth surface) 74, in the peripheral direction around the longitudinal axis L. A transverse cross section of the grip surface 74 which is orthogonal to the longitudinal axis L is formed into a substantially U-shape. That is, the outer peripheral surface of the second grasping portion 34 in the peripheral direction orthogonal to the longitudinal axis L is formed into an annular shape in which the fifth and sixth surfaces 72 and 74 cooperate. It is to be noted that at a position of the grip surface 74 which is close to the insertion section 12, there is formed a treatment device inlet (not shown) to project a treatment device from, for example, a distal face of the distal hard portion 22 through a channel (not shown).

When the first and second grasping portions 32 and 34 of the endoscope 10 are grasped with one hand (the left hand), the first surface 62 and the user facing surface 72 can face the operator. In a state where the first surface 62 and the user facing surface 72 face the user, the second surface 64 of the first grasping portion 32 is formed as a right side face disposed on operator's right side to the first surface 62, and the fourth surface 68 is formed as a left side face disposed on operator's left side to the first surface 62. It is to be noted that a projecting portion 70 is disposed on the third surface 66 formed between the second surface 64 on which the UD bending operation knob 36 is disposed and the fourth surface 68 on which an operator's palm abuts to grasp the first grasping portion 32.

It is to be noted that the third surface 66 of the first grasping portion 32 is present on a surface (a back surface) opposite to the first surface 62, and is continuous with the second surface 64 and the fourth surface 68. At a position of the first grasping portion 32 close to the second grasping portion 34, there is formed the projecting portion 70 that projects out from the sixth surface 74 of the second grasping portion 34 in a radial direction to the longitudinal axis L. That is, the third surface 66 is present on the side of the sixth surface 74 of the second grasping portion 34 which is opposite to the fifth surface 72, and is positioned to project out from the sixth surface 74 in the radial direction to the longitudinal axis L. Consequently, the projecting portion 70 of the first grasping portion 32 is formed not only by the third surface 66 but also by parts of the second surface 64 and the fourth surface 68, to project out from the sixth surface 74 of the second grasping portion 34 in the radial direction to the longitudinal axis L. Further, the projecting portion 70 has a projecting surface 70a that projects out from the sixth surface 74 of the second grasping portion 34 in the radial direction of the longitudinal axis L. The projecting surface 70a is formed in a boundary between the first grasping portion 32 and the second grasping portion 34, and between the second surface 64, the third surface 66 and the fourth surface 68.

On the second surface 64 of the first grasping portion 32, the UD bending operation knob 36 is disposed to be turnable and operable in a periaxial direction of the central axis CK. The UD bending operation knob 36 is disposed on the first surface 62 of the first grasping portion. 32 and on the second surface 64 that is adjacent to the third surface 66 opposite to the first surface 62 and is opposite to the fourth surface 68. Further, the UD bending operation knob 36 is operated by the user when the bending portion 24 of the insertion section 12 is bent. It is to be noted that the UD bending operation knob 36 is substantially formed into a star shape.

On the third surface 66, the first and second pressing valve units 52 and 54 are disposed. That is, the first and second pressing valve units 52 and 54 are disposed on the third surface 66 of the first grasping portion 32 which is adjacent to the second surface 64 in the peripheral direction and opposite to the first surface 62. The first pressing valve unit 52 is present in the third surface 66, i.e., the projecting portion 70, and is therefore positioned more distant from the longitudinal axis L than the sixth surface 74 at the position close to at least the second grasping portion 34.

On the fourth surface 68, the connector 42 for the universal cord is disposed. The universal cord 16 is extended from the connector 42 toward the user. That is, the universal cord 16 is extended toward a side opposite to the third surface 66. A lower surface 42a of the connector 42 is formed as a support portion on which the operator's index finger or the like is placed and supported, when the operator grasps the operation device 14.

It is to be noted that a boundary between the first surface 62 of the first grasping portion 32 and the user facing surface (the fifth surface) 72 of the second grasping portion 34 may be formed so that both the faces are continuous in the form of a substantially flat surface as shown in FIG. 1, or may be formed so that both the faces are continuous with each other at an angle, though not shown the drawing.

A peripheral length of an outer periphery of the second grasping portion 34 (a peripheral length in the periaxial direction of the longitudinal axis L) is adjusted to be shorter than a peripheral length of an outer periphery of the first grasping portion 32. In particular, a peripheral length of an outer periphery of the first grasping portion 32 at a position close to the second grasping portion 34 (a peripheral length in the periaxial direction of the longitudinal axis L) is adjusted to be longer than the peripheral length of the outer periphery of the second grasping portion 34. A peripheral length of an outer periphery of the first grasping portion 32 at a position away from the second grasping portion 34 (a peripheral length in the periaxial direction of the longitudinal axis L) may be adjusted to be longer or shorter than the peripheral length of the outer periphery of the second grasping portion 34.

Figure 3:
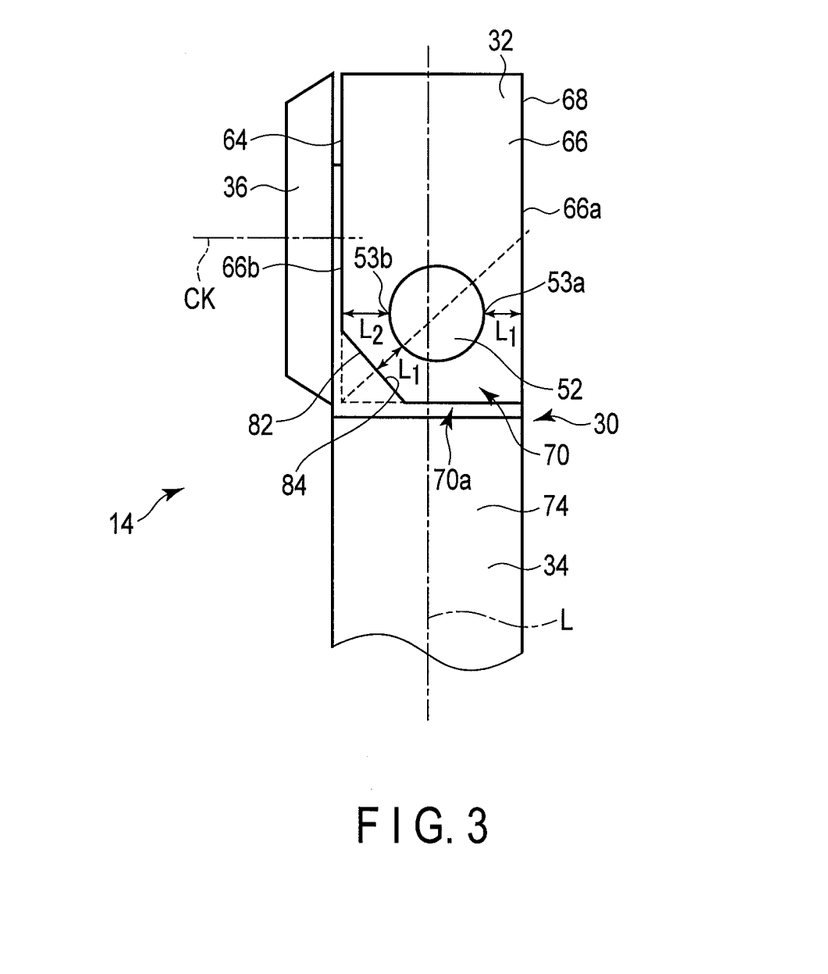
FIG. 3 is a schematic view schematically showing the operation device of the endoscope (the into-bore introduction device) according to the first embodiment.

As shown in FIG. 2 and FIG. 3, the projecting surface 70a of the projecting portion 70 has an inclined surface 82 at its position adjacent to the second surface 64. As shown in FIG. 3, the inclined surface 82 is formed at a position distant by as much as a predetermined distance from the pressing switch. Specifically, the inclined surface 82 includes an inclined edge portion (a first inclined edge portion) 84 at a position of an equal distance L1 from the first pressing valve unit 52 along the longitudinal axis L toward a side close to the insertion section 12, to the shorter distance (the shortest distance) L1 (L1<L2) in the distances L1 and L2 from edge portions 53a and 53b of the first pressing valve unit 52 to edge portions 66a and 66b of the third surface 66 in the peripheral direction to the longitudinal axis L. That is, in the first grasping portion 32, the inclined surface 82 having the inclined edge portion 84 is formed at a position distant by as much as the shortest distance L1 from the first pressing valve unit 52. As shown in FIG. 2 and FIG. 3, the inclined edge portion 84 forms a boundary between the third surface 66 and the inclined surface 82, and is present at an end portion of the inclined surface 82 which is close to the first pressing valve unit 52. It is to be noted that the whole inclined edge portion 84 does not have to be present at the position of the shortest distance L1 to the first pressing valve unit 52.

The inclined surface 82 of the projecting surface 70a of the projecting portion 70 according to this embodiment is formed between the second surface 64, the third surface 66 and the boundary of the first and second grasping portions 32 and 34. The inclined surface 82 is formed so that an amount of the inclined surface to project outside in the radial direction to the longitudinal axis L decreases with closer proximity to the insertion section 12 from the inclined edge portion 84 along the longitudinal axis L. Further, the inclined surface 82 of the projecting surface 70a according to this embodiment is formed as a circular surface formed between the second surface 64 and the third surface 66. The inclined surface 82 according to this embodiment is formed as a curved surface substantially orthogonal to the third surface 66 in FIG. 2. It is to be noted that as schematically shown in FIG. 3, the inclined surface 82 is preferably formed as a planar shape.

In this embodiment, there will be described a case where the bending portion 24 is bent in a U-direction and a D-direction, i.e., a case where the UD bending operation knob 36 is operated. However, the bending operation knob for RL 38 is preferably disposed at a position away from the second surface 64 to bend the bending portion 24 in an R-direction and an L-direction, and the bending portion 24 is preferably formed to bend in the R-direction or the L-direction by an operation of the RL bending operation knob 38.

Next, an operation of the endoscope 10 according to this embodiment will be described with reference to FIG. 1 to FIG. 4.

Figure 4:
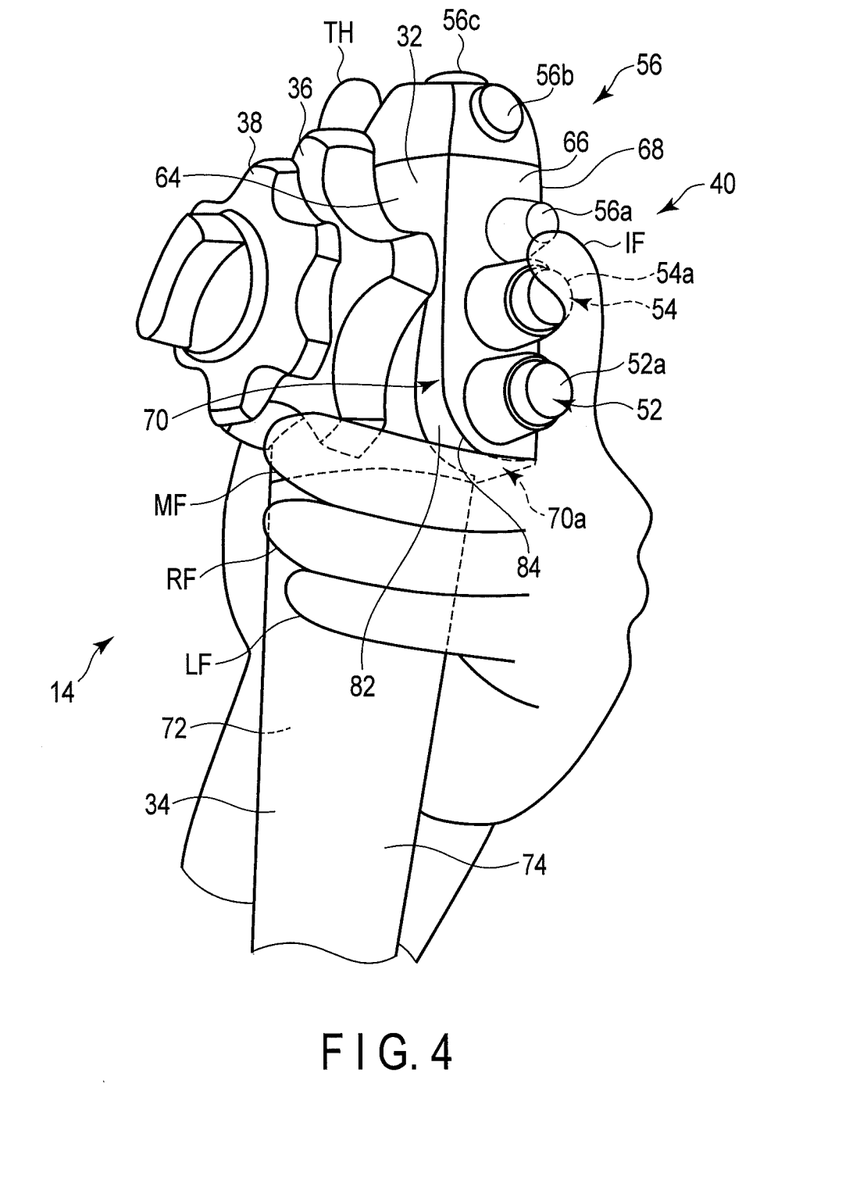
FIG. 4 is a schematic perspective view showing a state where the operation device of the endoscope (the into-bore introduction device) according to the first embodiment is grasped with a left hand.
Figure 5:
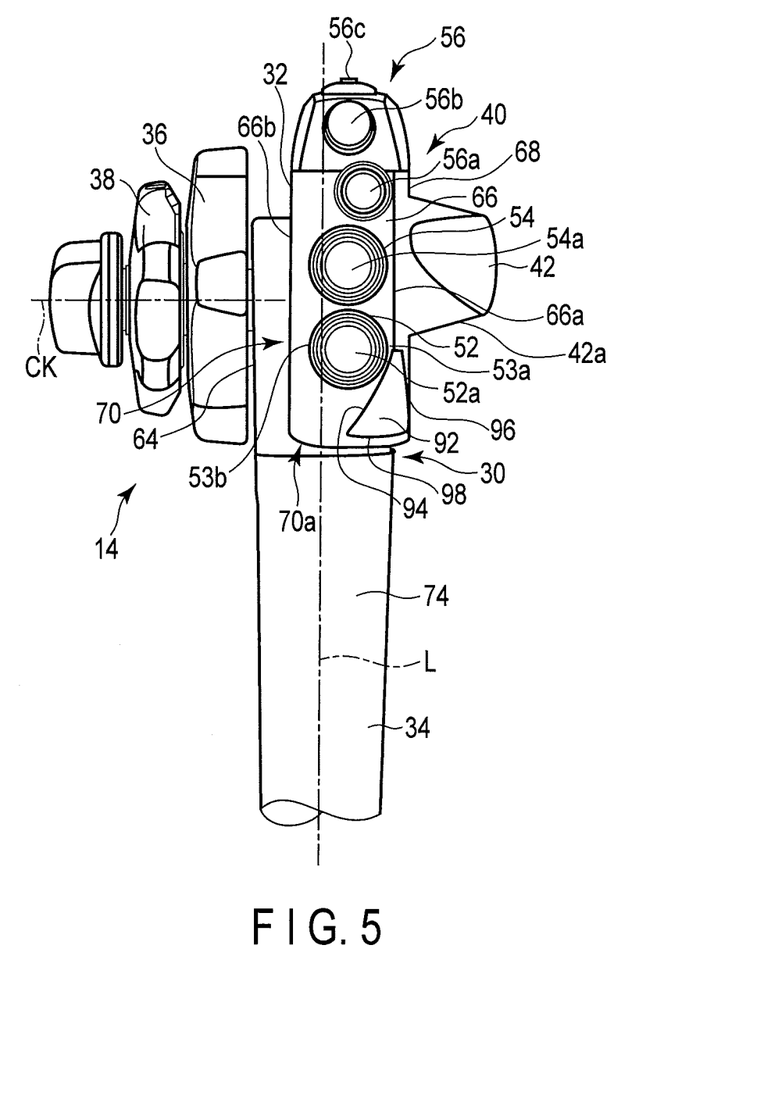
FIG. 5 is a schematic view showing an operation device of the endoscope (the into-bore introduction device) according to the second embodiment seen from the direction of the arrow II in FIG. 1.
Figure 6:
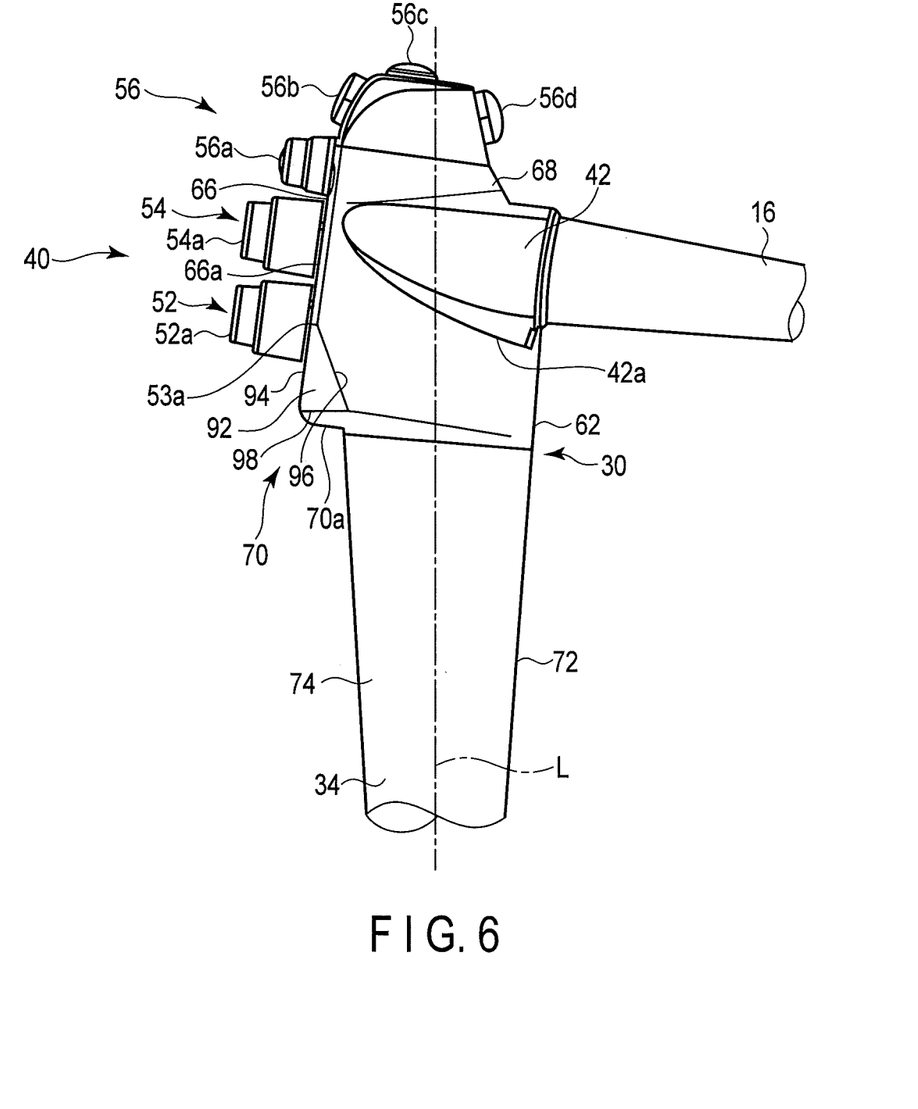
FIG. 6 is a schematic view showing the operation device of the endoscope (the into-bore introduction device) according to the second embodiment, and the operation device as seen from a side opposite to FIG. 1.

In a state where the first surface 62 of the first grasping portion 32 and the user facing surface (the fifth surface) 72 of the second grasping portion 34 are disposed to confront the user, the lower surface 42a of the connector 42 is disposed and supported on an index finger IF of the user's left hand, and a lower surface of the universal cord 16 is supported in the vicinity of a root of a thumb TH. The thumb TH is placed from the first surface 62 to the second surface 64 through a lower side of the universal cord 16. At this time, as shown in FIG. 4, the thumb TH can be placed in the vicinity of a switch 56d of the switch unit 56 disposed at a position close to the user or a convex portion 36a of the UD bending operation knob 36.

The index finger IF is placed at a position where a pressing member 52a of the first pressing valve unit 52 of the switch assembly 40 is operable, or placed at a position where a pressing member 54a of the second pressing valve unit 54 is operable. Furthermore, the index finger IF is placed on the switches 56a, 56b and 56c of the switch unit 56 of the switch assembly 40. A middle finger MF is placed at the position where the pressing member 52a of the first pressing valve unit 52 is operable, or placed at a position where the UD bending operation knob 36 is supportable.

It is to be noted that a thenar of the thumb TH in the user's left palm is present in the vicinity of each of the first surface 62 and the fourth surface 68 and on left side face of each of the fifth surface 72 and the sixth surface 74. In such states, the user grips the operation device 14 including the first and second grasping portions 32 and 34 with the left hand.

Although not shown in the drawing, the user holds the insertion section 12 with the right hand, and pushes the distal hard portion 22 of the insertion section 12 into a bore such as a body cavity to insert the tubular member 26 from the distal hard portion 22 of the insertion section 12.

For example, when the insertion section 12 is inserted into the bore of a large intestine or the like from an anus side toward a distal side, for example, a transverse colon or the like, the bending portion 24 is suitably bent in the U-direction and the D-direction. At this time, the user repeats an operation of turning the insertion section 12 grasped with the right hand in the periaxial direction of the longitudinal axis L or turning the UD bending operation knob 36 of the operation device 14 grasped with the left hand in a suitable direction to insert the insertion section 12 from a proximal side toward the distal side. When the bent state of the bending portion 24 is suitably held, the user holds the UD bending operation knob 36 not only with the thumb TH but also with, for example, the middle finger MF, a ring finger RF or the like.

When the bent state of the bending portion 24 is suitably held, i.e., when the UD bending operation knob 36 is supported to maintain its position, the UD bending operation knob 36 is supported with the middle finger MF or the ring finger RF while maintaining a state where the UD bending operation knob 36 is turned as much as a suitable amount with, for example, the thumb TH. Afterward, the thumb TH is released from the UD bending operation knob 36. At this time, in a case where the UD bending operation knob 36 is turned, the knob may be turned with the middle finger MF, the ring finger RF or the like, or may be turned with the thumb TH.

Specifically, in a case where the UD bending operation knob 36 is held with the middle finger MF, the middle finger MF is moved from, for example, a state where the middle finger is placed on the pressing member 52a of the first pressing valve unit 52 to the UD bending operation knob 36 as shown in FIG. 4. Further, the middle finger MF is moved to the UD bending operation knob 36 while moving the ring finger RF and a little finger LF away from the inclined surface 82. At this time, in a state where the middle finger MF is placed to abut on the projecting surface 70a of the projecting portion 70, the UD bending operation knob 36 can easily be supported. Therefore, the middle finger MF is placed to abut on the projecting surface 70a of the projecting portion 70, whereby the UD bending operation knob 36 can stably be held with the middle finger MF without unstably moving the middle finger.

Additionally, in a case where the UD bending operation knob 36 is held with the ring finger RF, for example, the index finger IF is moved to the vicinity of the pressing member 54a of the second surface 54 or the vicinity of the switch 56a of the switch unit 56, and the middle finger MF is placed on the pressing member 52a of the first pressing valve unit 52. In this case, the middle finger MF is moved, and the ring finger RF and the little finger LF are moved from the second grasping portion 34 toward the first grasping portion 32. At this time, the UD bending operation knob 36 is supported with the middle finger MF, and similarly, the UD bending operation knob 36 can easily be supported in a state where the ring finger RF is placed to abut on the projecting surface 70a of the projecting portion 70. Therefore, the ring finger RF does not unstably move, and the UD bending operation knob 36 can stably be held with the ring finger RF.

For an operation portion of a conventional endoscope, in a first grasping portion and a second grasping portion, there is a substantially rectangular projecting surface (stepped portion) in a boundary between a third surface of the first grasping portion and a sixth surface of the second grasping portion, and in a case where a UD bending operation knob is supported with the middle finger or the ring finger, the middle finger or the ring finger needs to be placed on the planar projecting surface of a projecting portion (a lower side of the projecting portion) which is substantially orthogonal to a longitudinal axis. Further, the projecting surface is rectangular, and hence three surfaces of a second surface, the third surface and the lower surface of the projecting portion form one projecting corner portion. In the case where the UD bending operation knob is supported, the projecting corner portion formed by the three surfaces close to the UD bending operation knob 36 interferes with an operation of the UD bending operation knob 36 with the middle finger or the ring finger.

Also in the operation device 14 according to this embodiment, the middle finger MF or the ring finger RF needs to be placed on the projecting surface 70a of the projecting portion 70 in the case where the UD bending operation knob 36 is supported. However, in the operation device 14 according to this embodiment, the inclined surface 82 is formed in the lower surface (the projecting surface) 70a of the projecting portion 70. Consequently, three surfaces of the second surface 64, the third surface 66 and the projecting surface 70a of the projecting portion 70 do not form the projecting corner portion. Therefore, in a case where the UD bending operation knob 36 is supported with the middle finger MF or the ring finger RF, the middle finger MF or the ring finger RF can be prevented from interfering with the projecting portion 70 at a position close to the UD bending operation knob 36. Therefore, in a case where the UD bending operation knob 36 is supported with the middle finger MF or the ring finger RF, no excessive force is applied to the finger. MF or RF, and the knob can easily be supported.

Additionally, in a case where the bending portion 24 is further bent from a state where the UD bending operation knob 36 is supported with the middle finger MF or the ring finger RF, the UD bending operation knob 36 might be turned with the middle finger MF or the ring finger RF. At this time, the inclined surface 82 is formed in the lower surface (the projecting surface) 70a of the projecting portion 70 as described above. Consequently, the three surfaces of the second surface 64, the third surface 66 and the projecting surface 70a of the projecting portion 70 do not form the projecting corner portion. Therefore, due to the inclined surface 82, no excessive force is applied to the finger MF or RF, and hence it is easy to turn the UD bending operation knob 36 with the finger MF or RF.

As described above, the endoscope 10 according to this embodiment can be considered as follows.

Differently from the operation portion of the conventional endoscope, in the operation device 14 of the endoscope 10 according to this embodiment, the inclined surface 82 is formed between the second surface and the third surface of the first grasping portion 32 on which the UD bending operation knob 36 is disposed. Consequently, for example, when the position of the UD bending operation knob 36 is held with the middle finger MF, the ring finger RF or the like, interference with the finger MF or RF can be prevented by the projecting portion 70. Consequently, for example, a user who has comparatively small hands can easily maintain the position of the UD bending operation knob 36, because interference with the finger MF or RF is prevented in the operation device 14 according to this embodiment. Needless to say, a user who has comparatively large hands can easily maintain the position of the UD bending operation knob 36, because interference with the finger MF or RF is prevented. Therefore, the user can perform an operation in a state where stress is decreased, when performing the operation of supporting the UD bending operation knob 36 with the middle finger MF or the ring finger RF.

In the operation device 14 according to this embodiment, in the case where the UD bending operation knob 36 is supported, the finger is placed to abut on the projecting surface 70a of the projecting portion 70, the finger MF or RF can be prevented from being unstably moved, and hence a bent state of the bending portion 24 can stably be supported.

Therefore, according to this embodiment, there can be provided the operation device 14 for the endoscope (the operation device for the into-bore introduction device) which enables the bending operation knob 36 to be easily turned to a suitable position, and the endoscope (the into-bore introduction device) 10 having the operation device 14.

It is to be noted that according to the endoscope 10 of this embodiment, a shape of a large part of the operation device 14 and a diameter of the bending operation knob 36 are unchanged for a user who has heretofore used the endoscope. Therefore, the user of the endoscope 10 according to this embodiment can maintain a usual operation feeling to the extent possible.

In this embodiment, an example of the endoscope 10 has been described. Although not shown in the drawing, it is also preferable to form an into-bore introduction device in which the illumination optical system and the observation optical system are removed from the endoscope 10.

In this embodiment, there has been described the example where the first pressing valve unit 52 is disposed close to the second grasping portion 34, i.e., the example where the shortest distance L1 or L2 is taken to the edge portion 66a or 66b of the third surface 66 from the edge portion 53a or 53b of the first pressing valve unit 52 as standard, but it is also preferable that in place of the first pressing valve unit (the air supply/water supply unit) 52, the second pressing valve unit (the suction unit) 54 is disposed close to the second grasping portion 34, or the switch unit 56 is disposed close to the second grasping portion 34.

Additionally, in this embodiment, there has been described the case where the distance L1 between the right edge portion 53a of the first pressing valve unit 52 and the edge portion 66a of the third surface 66 in FIG. 3 is smaller than the distance L2 between the left edge portion 53b of the first pressing valve unit 52 and the edge portion 66b of the third surface 66. In a case where the distance L2 is smaller than the distance L1 (L1>L2), the distance L2 is employed as the shortest distance, and the inclined surface 82 having the inclined edge portion 84 at a position distant by as much as the shortest distance L2 from the first pressing valve unit 52 is formed in the first grasping portion 32 as described above.

It is to be noted that the inclined surface 82 of the projecting portion 70 described in the first embodiment is formed on a second surface 64 side. It is also preferable that an inclined surface having about the same shape is formed on a fourth surface 68 side. At this time, the inclined surface 82 is formed between the third surface 66, the fourth surface 68, and the boundary of the first and second grasping portions 32 and 34. Further, the inclined surface 82 is formed as a circular surface formed between the third surface 66 and the fourth surface 68. The inclined surface 82 on the second surface 64 side may be formed or does not have to be formed.

Next, a second embodiment will be described with reference to FIG. 5 to FIG. 8. This embodiment is a modification of the first embodiment, the same members or members having the same functions as the members described in the first embodiment are denoted with the same signs wherever possible, and detailed descriptions thereof are omitted.

Figure 7:
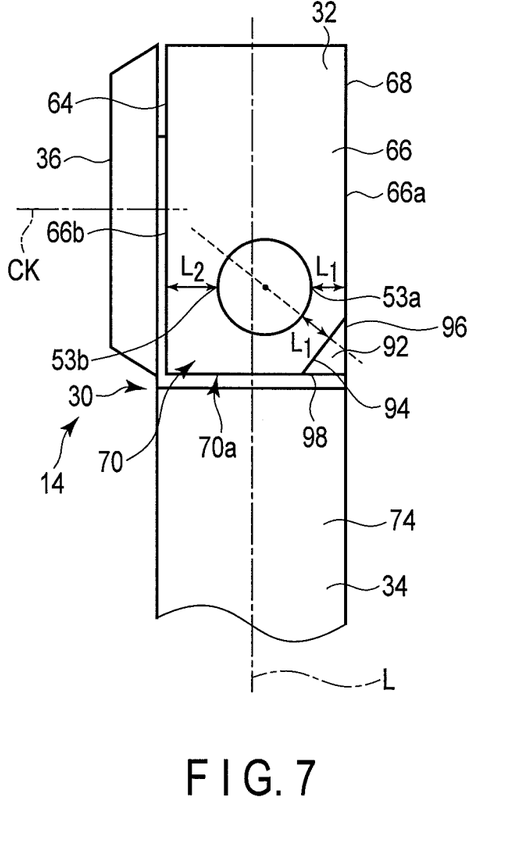
FIG. 7 is a schematic view schematically showing the operation device of the endoscope (the into-bore introduction device) according to the second embodiment.

As shown in FIG. 5 to FIG. 8, in an operation device 14 according to this embodiment, the inclined surface 82 described in the first embodiment is removed, and an inclined surface 92 having another shape is formed. The inclined surface 92 is formed between a third surface 66, a fourth surface 68 and a projecting surface 70a. As shown in FIG. 7, the inclined surface 92 includes a first inclined edge portion 94 at a position of an equal distance L1 from a first pressing valve unit 52 along a longitudinal axis L toward a side close to an insertion section 12, to the shorter distance (the shortest distance) L1 (L1<L2) in the distances L1 and L2 from edge portions 53a and 53b of the first pressing valve unit 52 to edge portions 66a and 66b of the third surface 66 in a peripheral direction to the longitudinal axis L. That is, in the first grasping portion 32, there is formed the inclined surface 92 having the inclined edge portion 94 at the position distant by as much as the shortest distance L1 from the first pressing valve unit 52. The inclined edge portion 94 is present at an end of the inclined surface 92. In the inclined surface 92, an amount of the inclined surface to project outside in a radial direction to the longitudinal axis L decreases with closer proximity to the insertion section 12 along the longitudinal axis L from the inclined edge portion 94. It is to be noted that the whole inclined edge portion 94 does not have to be present at the position of the shortest distance L1 to the first pressing valve unit 52.

The inclined surface 92 is formed by using a second inclined edge portion 96 formed in the fourth surface 68, and further, a third inclined edge portion 98 formed at a position closer to the projecting surface 70a than the second inclined edge portion 96, in addition to the inclined edge portion 94. The inclined surface 92 may be formed as a flat surface, or may be formed as a curved surface that projects in a normal direction to a plane defined by the inclined edge portions 94, 96, and 98.

The inclined surface 92 is not limited to the case where the inclined surface is formed by using the three inclined edge portions 94, 96, and 98. Although not shown in the drawing, for example, the third inclined edge portion 98 is also preferably formed in the projecting surface 70a so that an amount of a projecting portion 70 to project out to a sixth surface 74 of a second grasping portion 34 gradually decreases with closer proximity to the insertion section 12.

Next, an operation of an endoscope 10 according to this embodiment will be described with reference to FIG. 5 to FIG. 8.

Basically, the operation device 14 can be grasped to be operated in the same manner as described in the first embodiment.

Figure 8:
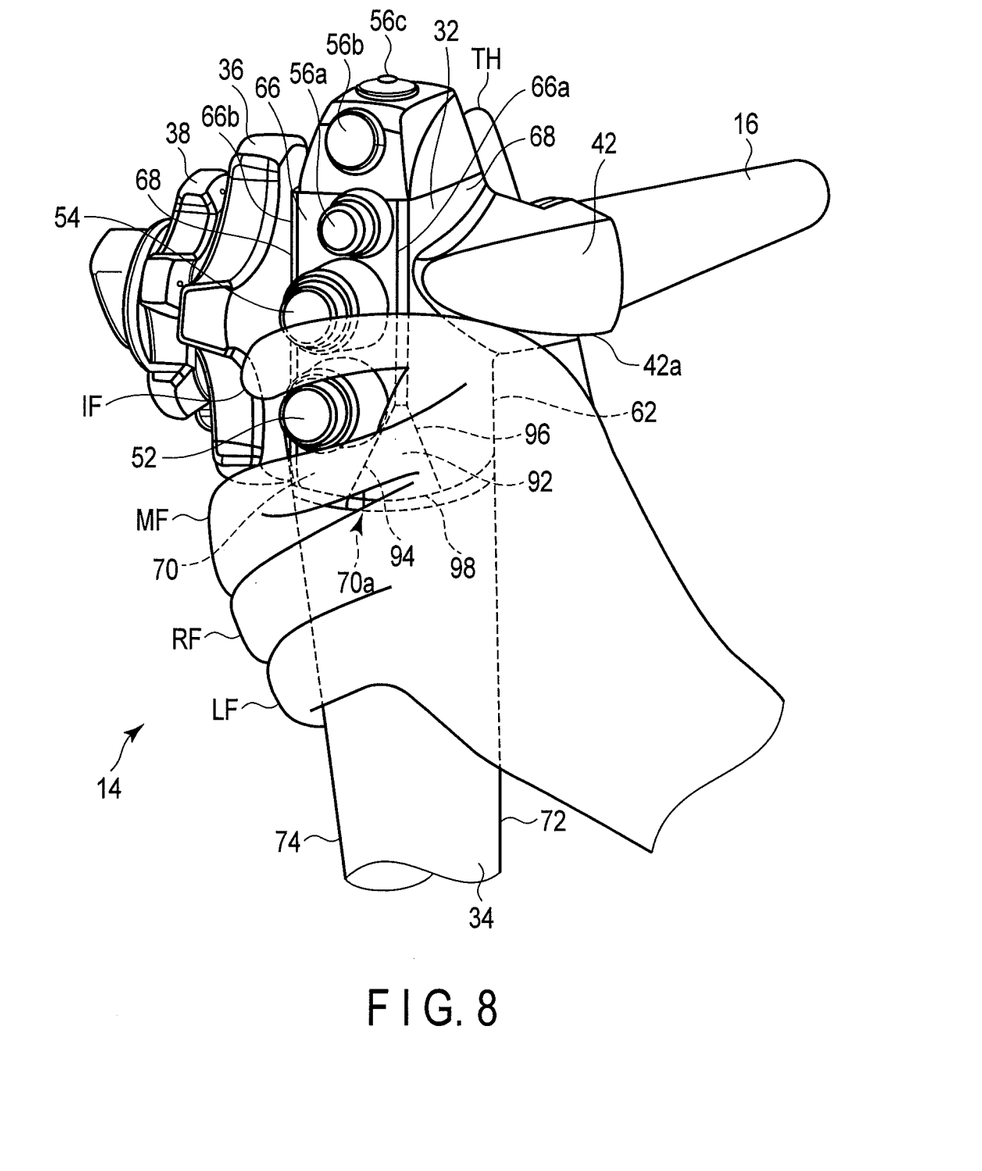
FIG. 8 is a schematic perspective view showing a state where the operation device of the endoscope (the into-bore introduction device) according to the second embodiment is grasped with a left hand.

In a state where a first surface 62 of a first grasping portion 32 and a user facing surface (a fifth surface) 72 of the second grasping portion 34 are disposed to confront a user, as shown in FIG. 8, a lower surface 42a of a connector 42 is disposed and supported on an index finger IF of the user's left hand, and a lower surface of a universal cord 16 is supported in the vicinity of a root of a thumb TH. The thumb TH is placed from the first surface 62 to a second surface 64 through a lower side of the universal cord 16. At this time, the thumb TH can be placed in the vicinity of a switch 56d of a switch unit 56 disposed at a position close to the user or a convex portion 36a of a UD bending operation knob 36. A thenar of the thumb TH in the user's left palm is present in the vicinity of each of the first surface 62 and the fourth surface 68 and on a left side face of each of the fifth surface 72 and the sixth surface 74.

The index finger IF is placed at a position where a pressing member 52a of the first pressing valve unit 52 of a switch assembly 40 is operable, or placed at a position where a pressing member 54a of a second pressing valve unit 54 is operable. Furthermore, the index finger IF is also placed on a switch 56a of the switch unit 56 of the switch assembly 40.

A middle finger MF is placed at the position where the pressing member 52a of the first pressing valve unit 52 is operable, or placed at a position where the UD bending operation knob 36 is supportable.

In an operation portion of a conventional endoscope, one projecting corner portion is formed by using three surfaces of a third surface, a fourth surface and a projecting surface (a lower surface of a projecting portion). In a case where a UD bending operation knob is supported, the projecting corner portion formed by the three surfaces disposed away from a UD bending operation knob 36 is interfered when the UD bending operation knob is operated with the middle finger or the ring finger.

Also in the operation device 14 according to this embodiment, the middle finger MF or a ring finger RF needs to be placed on the projecting surface 70a of the projecting portion 70 in a case where the UD bending operation knob 36 is supported. However, in the operation device 14 according to this embodiment, the inclined surface 92 is formed continuously with the lower surface (the projecting surface) 70a of the projecting portion 70. Consequently, the projecting corner portion is not formed by using three surfaces of the third surface 66, the fourth surface 68 and the projecting surface 70a of the projecting portion 70. In consequence, when the UD bending operation knob 36 is supported with the middle finger MF or the ring finger RF, the middle finger MF or the ring finger RF can be prevented from interfering with the projecting portion 70 at a position away from the UD bending operation knob 36. Therefore, in the case where the UD bending operation knob 36 is supported with the middle finger MF or the ring finger RF, no excessive force is applied to the finger MF or RF, and the knob can easily be supported. Consequently, the root of the finger MF or RF can be placed closer to the UD bending operation knob 36 than in the operation portion of the conventional endoscope. Additionally, also when the inclined surface 92 according to this embodiment is formed as the curved surface, the surface is curved to such an extent that the surface can substantially be seen as a flat surface, and the finger MF can be prevented from being stuck on the surface.

Additionally, in a case where a bending portion 24 is further bent from the state where the UD bending operation knob 36 is supported with the middle finger MF or the ring finger RF, the UD bending operation knob 36 might be turned with the middle finger MF or the ring finger RF. At this time, the inclined surface 92 is formed continuously with the lower surface (the projecting surface) 70a of the projecting portion 70 as described above. Consequently, the three faces of the third surface 66, the fourth surface 68 and the projecting surface 70a of the projecting portion 70 do not form the projecting corner portion. Therefore, due to the inclined surface 92, no excessive force is applied to the finger MF or RF, and hence it is easy to turn the UD bending operation knob 36 with the finger MF or RF.

Therefore, according to this embodiment, in the same manner as described in the first embodiment, there can be provided the operation device 14 for the endoscope (the operation device for an into-bore introduction device) by which it is easy to support a turned position of the bending operation knob 36 at a suitable position, and the endoscope (the into-bore introduction device) 10 having the operation device 14.

It is to be noted that as shown in FIG. 7, the inclined surface 92 described in the second embodiment is formed on a fourth surface 68 side. It is also preferable to form an inclined surface having about the same shape on a second surface 64 side. At this time, the inclined surface 92 on the fourth surface 68 side may be formed, or does not have to be formed.

Figure 9:
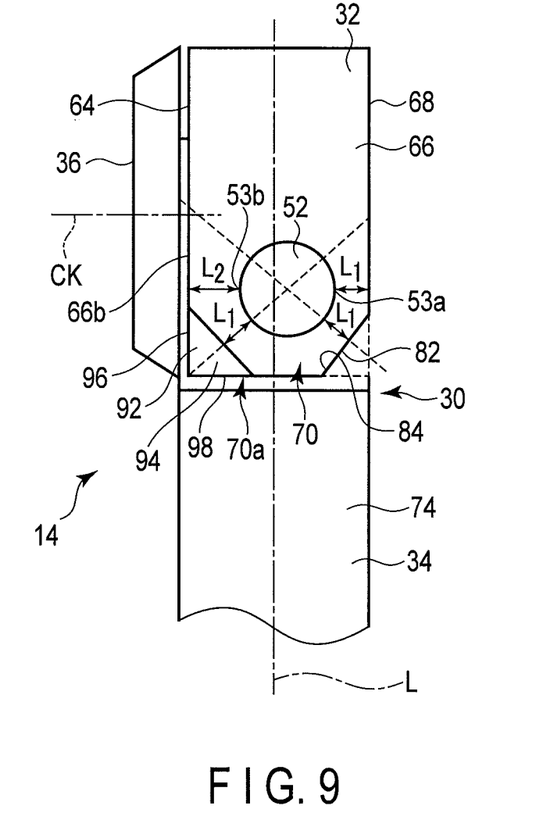
FIG. 9 is a schematic view schematically showing an operation device of an endoscope (an into-bore introduction device) according to a modification of the first and second embodiments.

Additionally, as shown in FIG. 9, it is also preferable that the inclined surface 82 described in the first embodiment is formed on a fourth surface 68 side (at a position away from a UD bending operation knob 36) and that the inclined surface 92 described in the second embodiment is formed on a second surface 64 side (at a position close to the UD bending operation knob 36).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An operation device for an into-bore introduction device, comprising:
   a grasping section that is connected to a proximal portion of an insertion section to be inserted into a bore, and is to be grasped by an operator to operate the insertion section;
   a bending operation knob that is disposed on the grasping section and that bends a bending portion of the insertion section;
   a projecting portion that projects from the grasping section radially in relation to a longitudinal axis of the grasping section, the projecting portion being formed on a third surface between a second surface on which the bending operation knob is disposed and a fourth surface, which is on an opposite side of the grasping section from the second surface, the projecting portion including a projecting surface, which is a surface of the projecting portion that is closest to the insertion section;
   a pressing switch that is disposed on the projecting portion and that operates the insertion section; and
   a corner portion that is disposed at an intersection between the projecting portion and the fourth surface,
   an inclined surface that is formed at a position of the projecting surface of the projecting portion adjacent to the second surface and a position of an equal distance from the pressing switch toward a side close to the insertion section along the longitudinal axis, to the shortest distance defined between an edge portion in the direction peripheral to the longitudinal axis and the pressing switch on a surface between the second surface and the fourth surface, the inclined surface being a circular surface that is between the second surface and the projecting surface and convex in a direction away from the pressing switch.

2. The operation device according to claim 1, wherein:
the grasping section includes:
a first grasping portion that includes a first surface, the second surface, the third surface, and the fourth surface cooperating along a peripheral direction of the longitudinal axis to form an annular shape; and
a second grasping portion that is disposed on a side closer to the insertion section than the first grasping portion, and that includes a fifth surface disposed continuously with the first surface, and a sixth surface disposed in the peripheral direction of the longitudinal axis and cooperating with the fifth surface to form the annular shape in the direction peripheral to the longitudinal axis.

3. The operation device according to claim 2, wherein the bending operation knob is disposed on the second surface of the first grasping portion, the second surface being adjacent to the first surface and the third surface opposite to the first surface, the second surface being opposite to the fourth surface.

4. The operation device according to claim 3, wherein:
the projecting portion is formed by using the third surface, a part of the second surface, and a part of the fourth surface, and
a position of the projecting portion which is close to the second grasping portion projects out from the sixth surface of the second grasping portion in the radial direction to the longitudinal axis.

5. The operation device according to claim 4, wherein:
the pressing switch is disposed on the third surface at a position of the pressing switch that is close to the second grasping portion.

6. The operation device according to claim 5, wherein the inclined surface includes a first inclined edge portion which is disposed in a position between the projecting portion and the second surface, and which is disposed at a position of an equal distance from the pressing switch toward a side close to the insertion section along the longitudinal axis, to the shortest distance.

7. The operation device according to claim 6, wherein the inclined surface is formed between one of the second surface and the fourth surface, the third surface, and a boundary of the first and second grasping portions, and is substantially orthogonal to the third surface.

8. The operation device according to claim 6, wherein:
the projecting portion includes a projecting surface that is formed in a boundary between the first grasping portion and the second grasping portion and projects out from the sixth surface of the second grasping portion in the radial direction of the longitudinal axis, and
the inclined surface has a circular surface formed between the second surface and the projecting surface.

9. The operation device according to claim 6, wherein:
the projecting portion includes a projecting surface that is formed in a boundary between the first grasping portion and the second grasping portion and projects out from the sixth surface of the second grasping portion in the radial direction of the longitudinal axis, and
the inclined surface is formed between the second surface, the third surface, and the projecting surface.

10. The operation device according to claim 6, wherein:
the projecting portion includes a projecting surface that is formed in a boundary between the first grasping portion and the second grasping portion and projects out from the sixth surface of the second grasping portion in the radial direction of the longitudinal axis, and
the inclined surface is formed between a second inclined edge portion formed in at least one of the second surface and the fourth surface and a third inclined edge portion formed in the projecting surface or at a position closer to the projecting surface than the second inclined edge portion, in addition to the first inclined edge portion.

11. An into-bore introduction device comprising:
the operation device for the into-bore introduction device according to claim 1; and
an insertion section that includes a bending portion, and that is extended to the grasping section along the longitudinal axis.

12. The operation device according to claim 1, wherein the corner portion is provided opposite the inclined surface.

* * * * *